United States Patent [19]
Denkewicz, Jr. et al.

[11] Patent Number: 6,093,422
[45] Date of Patent: Jul. 25, 2000

[54] BIOCIDAL COMPOSITIONS FOR TREATING WATER

[75] Inventors: Raymond P. Denkewicz, Jr., Warwick, R.I.; Ernest E. Senderov, Conshohocken, Pa.; Joseph W. Grenier, North Providence, R.I.

[73] Assignee: Zodiac Pool Care, Inc., Smithfield, R.I.

[21] Appl. No.: 09/097,643

[22] Filed: Jun. 16, 1998

Related U.S. Application Data

[60] Provisional application No. 60/072,283, Jan. 23, 1998.

[51] Int. Cl.$^7$ .......................... A01N 59/16; A01N 59/20; A01N 43/04
[52] U.S. Cl. .......................... 424/618; 424/619; 424/630; 424/632; 424/634; 424/635; 424/641; 514/54; 514/55
[58] Field of Search .................................... 210/748, 764, 210/749; 424/618, 619, 630, 632, 634, 635, 641; 514/54, 55

[56] References Cited

U.S. PATENT DOCUMENTS

| | | | |
|---|---|---|---|
| 2,076,917 | 4/1937 | Pfuetzer et al. | 71/4 |
| 2,140,401 | 12/1938 | Fink | 210/23 |
| 2,400,863 | 5/1946 | Gelfand | 167/16 |
| 3,296,069 | 1/1967 | Kowalski | 167/33 |
| 3,533,940 | 10/1970 | Peniston et al. | 210/52 |
| 3,708,578 | 1/1973 | Da | 424/141 |
| 3,821,369 | 6/1974 | Brink, Jr. et al. | 424/141 |
| 3,888,684 | 6/1975 | Little | 106/15 |
| 4,227,899 | 10/1980 | Meny et al. | 55/279 |
| 4,229,410 | 10/1980 | Kosti | 422/28 |
| 4,424,346 | 1/1984 | Hall et al. | 536/20 |
| 4,525,410 | 6/1985 | Hagiwara et al. | 428/198 |
| 4,605,623 | 8/1986 | Malette et al. | 435/240 |
| 4,659,700 | 4/1987 | Jackson | 514/55 |
| 4,911,898 | 3/1990 | Hagiwara et al. | 423/118 |
| 5,015,632 | 5/1991 | Nelson | 514/55 |
| 5,149,354 | 9/1992 | Delaney | 71/67 |
| 5,332,511 | 7/1994 | Gay et al. | 210/755 |
| 5,373,025 | 12/1994 | Gay | 514/642 |
| 5,407,816 | 4/1995 | Bringi et al. | 435/123 |
| 5,482,932 | 1/1996 | Thompson | 514/54 |
| 5,490,978 | 2/1996 | Spaltro et al. | 424/49 |
| 5,541,150 | 7/1996 | Garris | 504/151 |
| 5,561,167 | 10/1996 | Matsumoto et al. | 521/31 |
| 5,632,901 | 5/1997 | Engström | 210/724 |
| 5,632,904 | 5/1997 | Samad et al. | 210/704 |
| 5,641,413 | 6/1997 | Momont et al. | 210/704 |

FOREIGN PATENT DOCUMENTS

| | | |
|---|---|---|
| 0 494 373 A1 | 7/1992 | European Pat. Off. . |
| 8268821 | 10/1996 | Japan . |
| 964766 | 3/1997 | South Africa . |
| WO 97/37939 | 10/1997 | WIPO . |

OTHER PUBLICATIONS

International Search Report in corresponding International Application No. PCT/US98/26773.

Grenier and Denkewicz, "Improved Test Medium for the Evaluation of Algaecides & Algaestats for Swimming Pools," Published in Jun. 1998 at the 2nd Annual Chemistry Symposium, Chicago, Illinois (held Nov. 11, 1997).

*Primary Examiner*—Jose' G. Dees
*Assistant Examiner*—Alton Pryor
*Attorney, Agent, or Firm*—Bruce D. Gray; Dean W. Russell; Kilpatrick Stockton LLP

[57] ABSTRACT

The present invention is directed to a biocidal water treatment composition, water treatment apparatus, and method of treating water to reduce levels of pathogens. The composition contains sources of copper, zinc, and silver metal ions within a crosslinked polymer matrix. Examples of these ion sources include copper sulfate, zinc sulfate, and silver nitrate. An example of the crosslinked polymer matrix is crosslinked chitosan, which also serves to clarify the water and release the metal ions over time. The product is easy to manufacture, and allows the use of decreased halogen sanitizer, as well as decreased copper ion, thereby decreasing the likelihood of staining. The product simultaneously provides good bactericidal and algaecidal properties, despite low levels of copper ion and low chlorine levels.

46 Claims, No Drawings

BIOCIDAL COMPOSITIONS FOR TREATING WATER

BACKGROUND OF THE INVENTION

This application claims priority to Application No. 60/072,283 filed as a provisional application on Jan. 23, 1998, by Raymond P. Denkewicz, Ernest E. Senderov and Joseph E. Grenier entitled "Biocidal Compositions for Treating Water."

FIELD OF THE INVENTION

The present invention relates to a composition, water treatment system, and method for treating bodies of water to inhibit microbial, algal, and fungal growth. In particular the present invention relates to the treatment of recirculating bodies of water, such as swimming pools, hot tubs, spas, fountains, ponds, cooling system water, and water contained in humidification systems, to inhibit, reduce or prevent the growth of microorganisms such as bacteria, algae, fungi, and viruses. More particularly, the invention relates to a metal salt-based composition for maintaining swimming pool, spa, hot tub, or other water in a pathogen-free and aesthetically acceptable state at reduced chlorine levels, while simultaneously reducing both the formation of stains on pool surfaces and the turbidity of water. However, the invention is also applicable to any body of water, whether for industrial, agricultural, or recreational use, that is subject to the growth of microorganisms.

DESCRIPTION OF BACKGROUND AND RELATED ART

Bodies of water, and in particular those bodies of water that are recirculated, provide fertile breeding grounds for algae, bacteria, viruses, fungi, and other pathogens if the water is left untreated. Microbial contamination can create a variety of problems, ranging from aesthetic unpleasantries, such as slimy green water, to serious health risks such as fungal, bacterial, or viral infections.

Swimming pools and other recirculating bodies of water used for recreational purposes, such as hot tubs or spas, are particularly conducive to microbial growth, as users introduce new pathogens as they bathe or swim.

Ponds, such as garden or fish ponds, often desirably contain some microorganisms as nutrients for their inhabitants. In some circumstances, however, growth of undesirable and even desirable microorganisms can become uncontrolled, reducing the ability of the pond to support other desirable organisms by increasing the pond's biological oxygen demand or BOD. Industrial or agricultural ponds, used for storing water used in manufacturing or agricultural applications, are also subject to uncontrolled growth of microorganism that can form sufficient biomass to become entrained with the water and interfere with the operation of industrial or agricultural machinery or processes.

Recirculating water cooling systems, such as natural draft cooling towers, recycle heated cooling water by contacting the water with an unsaturated gas, such as air, thereby cooling the water by evaporation, and can also be used to cool the air, which may then be used to ventilate areas inhabited by humans or other animals. Microorganisms can be introduced by the cooling surfaces of the device, or by the air that comes into contact with the water. Their growth, if allowed to go unchecked, can result in sufficiently dense masses of organic material to clog or foul water flow lines and valves, contribute to rot or corrosion, and decrease cooling efficiency.

Similarly, humidification systems, where water is sprayed into warm, unsaturated air to cause essentially adiabatic mass transfer of some of the water to the air in the form of water vapor, can also result in transfer of pathogenic microorganisms from the water to the air. Since this humidified air is often intended for breathing by humans or other animals, the result can be infection by the contaminants transferred to the air from the water.

While many of these microbial contaminants that can grow in untreated water are harmless, others can be pathogenic and lead to outbreaks of infectious disease. One of the most common waterborne disease is dermatitis, which can be caused by an overgrowth of *Pseudomonas aeruginosa* bacteria. Other common diseases that can result from pathogens in bathing or swimming water include bacterial gastroenteritis, external otitis (swimmer's ear), candidia and *tinea pedis* (athlete's foot). More serious illnesses, such as *Legionella pneumophila* (Legionnaire's disease), may also spread through contaminated swimming pools and spas, as well as through contact of contaminated cooling water with air used in building ventilation systems.

Halogens, in particular chlorine and bromine, have traditionally been used to combat microbial contamination of swimming pools, hot tubs, spas, etc. As strong oxidizing agents, halogens are effective in destroying and preventing the growth of a wide variety of organisms. They can be utilized in a variety of forms, including chlorine gas, liquid chlorine, and more typically chlorine- or hypochlorite-releasing agents. Calcium hypochlorite, $Ca(OCl)_2$, is commonly used to treat public swimming pools, and contains 70% available chlorine. Chlorinated isocyanurates, including dichlor and trichlor and their salts, are commonly used to treat private swimming pools. Alternatively, chlorine can be generated by electrolysis for use in swimming pools. In combination with other measures designed to limit the build-up of organic matter in pool water, a constant adequate level of available chlorine of 1 to 3 ppm is generally required to maintain a pool in a pathogen-free state.

The use of chlorine, hypochlorite, and chlorine- and hypochlorite-generating water treatment chemicals (hereinafter referred to as "chlorine"), and in particular pool, hot tub, and spa treatment chemicals, presents numerous problems, however. Most notably, chlorine has been associated with health risks ranging from mild skin and eye irritation to an increased incidence of cancer. Chlorinated products, resulting from the reaction of chlorine with organic matter present in pool water, are thought to produce these adverse effects. In particular, chlorinated hydrocarbons, produced in pool water and then ingested by bathers, are suspected carcinogens.

Other disadvantages associated with the use of chlorine as a biocide relate to its performance and cost. The biocidal activity of chlorine is very sensitive to the environment in which it is used. Specifically, chlorine is only effective as a biocide within a narrow pH range. Relatively small variations in pH, therefore, can cause a loss of biocidal activity. Chlorine's sensitivity necessitates both careful monitoring of pool water pH as well as the adoption of pH-corrective measures to maintain the pH in a suitable range. Exposure to sunlight can also effect biocidal activity, as sunlight destroys hypochlorous acid formed from the hydrolysis of $Cl_2$. This necessitates the addition of stabilizers to prevent the loss of biocidal activity from this source. The use of a strong oxidizing agent, such as chlorine, can also cause aesthetic problems, including bleaching and discoloration of swimwear, greenish hair, etc. In addition, the increasing cost of chlorine-based pool chemicals makes their use in large quantities less favorable economically.

For these and other reasons, it is desirable to reduce the quantity of chlorine needed and used to achieve an acceptably low level of microorganisms in swimming pools, hot tubs, spas, etc. A variety of compositions have been suggested for this purpose, including compositions containing heavy metal ions such as copper, silver, zinc, and nickel. Metal ions are known biocides, and have been provided as metal salt-based compositions for the treatment of swimming pools and other bodies of water. In particular, water soluble inorganic salts of copper, such as copper sulfate, copper nitrate, and copper chloride, have been suggested for use as algaecides and/or bactericides for the treatment of water.

The use of copper or copper ion sources, however, presents several disadvantages. Copper ions react with naturally occurring anions in alkaline or near-alkaline water, and precipitate as insoluble salts of, e.g., carbonate, oxide, and/or hydroxide. Copper precipitation is also sensitive to pH. Precipitation leads to a loss of biocidal activity as the copper ions are no longer available in solution. Precipitation also causes aesthetic problems including turbidity of water and the formation of stains on surfaces, such as pool surfaces. Conventional wisdom has been that, at copper levels sufficiently high to have a significant biocidal effect, it is necessary to add complexing agents having ligands that coordinate with the copper ion in order to shield the ion from the anions in solution thereby keeping it from precipitating and available for biocidal action. See U.S. Pat. No. 5,632,904. A variety of sequestering agents have been used to enhance the stability of the copper ions in solution in this way. For example, EDTA (ethylene diamine tetra acetic acid), citric acid, and salicylic acid are known to stabilize copper ions in solution by sequestering them. However, these sequestrants can be broken down in the presence of oxidizing agents such as chlorine, which will generally still be necessary in some quantities despite the use of metal biocides. In addition, sequestrants can bind metal ions so strongly that the biocidal activity of the ions is inhibited. These factors render the use of sequestrant-containing biocides complicated and difficult for the average pool user.

In addition, copper salt biocides are more effective against algae than against bacteria and other pathogens. In order to obtain significant bactericidal activity from copper salt biocides, unreasonably high copper concentrations are necessary. As a result, copper salt containing biocides are generally suitable as algaecides, requiring the use of additional biocides to control bacteria and other pathogens.

Preparation of copper-salt biocides, including copper-salt biocides containing salts of other metal ions, such as silver and zinc salts, has also proven problematic. Specifically, the failure to adhere to an ordered sequence of additions in the preparation of known copper, silver, and zinc biocides has produced uncontrollable frothing as well as the formation of black deposits during formation or compounding of the biocidal composition.

There is a need, therefore, to improve compositions of this type, and particularly, to provide metal biocide compositions for treating recirculating bodies of water that permit maintenance of the water in a pathogen-free and aesthetically acceptable state at reduced chlorine levels, while simultaneously reducing or eliminating the problems of staining and turbidity that have become associated with the use of metal biocides without the need for sequestrants, as discussed above.

It is, therefore, an object of the present invention to provide an improved metal salt-based composition for treating recirculated bodies of water to simultaneously inhibit microbial and algal growth and to reduce, as a result of the action of these combined metals, the amount of chlorine necessary to maintain the water in a pathogen-free and aesthetically acceptable state.

It is another object of the present invention to provide a metal salt-based composition for treating water that provides copper, zinc, and silver ions in solution, but maintains copper as well a silver at concentration levels below the levels that will result in staining of surfaces, such as pool surfaces, that contact the water, and also reduces or eliminates turbidity of the water, without requiring sequestration of the copper ions that are in solution.

It is a further object of the present invention to provide a composition that has a simple method of manufacture that eliminates the need for any special order of addition, as well as the need for heating and/or cooling steps or applying pressure and that does not result in frothing or black deposits forming during manufacture.

It is a further object of the present invention to produce a metal-salt based composition that quickly provides and effectively maintains concentrations of metal ions that reduce, control, limit, or inhibit the growth of microorganisms in water.

It is a further object of the present invention to provide a water treatment composition, a water treatment system containing the composition, and a method for using the composition that is characterized by ease of handling, simplicity of use, long lasting effects (in the sense that the biocidally active ions remain present and active in the water for several months), and effectiveness at producing clear, pathogen-free water in swimming pools, hot tubs, spas, fountains, ponds, humidifiers, cooling systems, and any other applications when microbial contaminants (e.g., bacteria, algae, fungi, viruses, etc.) are problems.

It is a further object of the present invention to provide a solid metal salt-based water treatment composition that can be easily solidified without expansion or shrinkage, and that can be easily molded into different shapes, such as tablets, sticks, or pellets, or stuffed into various holders, such as tubes.

It is a further object of the present invention to provide a metal salt based water treatment composition that reduces or eliminates the need for commonly used added metal ion sequestrants in the water (such as EDTA, citric acid, or high levels of ionic polymers, etc.), while avoiding staining of the surfaces in contact with the water, and turbidity of the water.

These and other objects and advantages, as well as the nature and proper use of the invention, will be readily apparent to those skilled in the art from the following description and claims.

SUMMARY OF THE INVENTION

The objects and advantages described above are provided by the present invention, which is directed to a novel composition for treating bodies of water, in particular recirculating bodies of water, to kill, remove, or inhibit the growth of microorganisms, including bacteria, fungi, algae, viruses, and other microorganisms at reduced chlorine levels (i.e., at chlorine levels below those needed to maintain an acceptable reduction of microorganism growth when halogens, such as chlorine or hypochlorite, or compounds that produce these, are used as the primary or sole biocide or sanitizers) and at copper levels well below the threshold at which surface staining occurs in most recreational or industrial waters. The composition is formed by mixing sources of copper, silver, and zinc ions, and in one embodiment of the invention, one or more crosslinkable polymers, and a crosslinking agent, such as sulfuric acid. The zinc and silver ion sources are present in such quantities as to provide sufficient zinc and silver ions to the water and to achieve an acceptable biocidal result to permit reduction in the amount of copper ion required. Specifically, copper is used at levels that are sufficiently low that copper staining does not occur, yet an acceptable level of reduction in microorganism growth is maintained in the water. In addition, the presence of this low level of copper ion in solution eliminates the need for added sequestrants, since at the copper concentrations made possible by the inclusion of zinc and silver, copper staining will not occur, and sequestrants are unnecessary. Additional components of the composition, e.g., the polymer matrix, such as crosslinked chitosan, need not be present in amounts sufficient to provide any significant sequestering or flocculating effect under existing water conditions, and may be used in amounts below those at which any sequestering or flocculating effect is measurable.

The composition, water treatment system, and method of treating water are discussed in more detail below by reference to swimming pool water, however it will be understood that these can be used advantageously in hot tubs, spas, ponds, water cooling systems, humidification systems, and in any water system where microorganism growth is desirably controlled. Accordingly, the discussion below is applicable to these systems as well. In particular, the invention can be used advantageously in systems using recirculated water and in particular in systems where the amount of oxidizing biocide, like chlorine or hypochlorite, is desirably controlled or limited and where staining by copper biocides may also cause problems.

This combined effect of silver ions and zinc ions in permitting a reduction of the copper and chlorine levels is unexpected, and is used in the present invention to provide a biocidally effective composition that advantageously avoids the staining of surfaces that contact the water, but not by adding large quantities of organic sequestrants, which can later be broken down by the strong oxidizing agents in the water, requiring constant replenishment (which generally is accomplished by adding additional sequestrant complexed with yet more copper ion). Instead, the present invention makes use of the surprising effect of silver and zinc ions, in conjunction with copper ions, in maintaining a high degree of biocidal effectiveness, particularly algaecidal effectiveness and bactericidal effectiveness, despite substantially decreased copper ion concentrations. This allows the copper ion concentration in the water to be maintained at a sufficiently low level that precipitation is minimized or eliminated entirely, and in any case, staining is avoided. Accordingly, the composition of the present invention provides a metal salt-based biocide that represents a significant advance over what has previously been available in the art. One significant advantage of the present invention is that it provides effective destruction and/or growth inhibition of both bacteria and algae, and is not limited in its effectiveness to one or the other.

As indicated above, the relative abundance of zinc ion source and silver ion source allow the use of an amount of copper ion source significantly lower than would have been thought to be required, and provides good bactericidal and algaecidal control while still reducing staining. The ratio of zinc ion source to copper ion source (by weight based on zinc and copper atoms) can range from about 0.5:1 to about 4:1. The ratio of silver ion source to copper ion source (by weight based on silver and copper atoms) can range from about 0.05:1 to about 2:1. As an example, a ratio of zinc ion source to copper ion source of 2.3:1 and a ratio of silver ion source to copper ion source of 0.6:1 have been found to be suitable.

In an embodiment of the invention where the composition is provided as a solid mixture of the metal ion sources and a soluble polymer matrix, the composition is formed by mixing sources of the various metal ions, adding one or more crosslinkable polymers, and as a final step, adding a crosslinking agent. The resulting composition may then be formed in any desired shape, and dried to a solid at room temperature using known methods of molding, extrusion, etc. The composition solidifies upon drying without shrinkage or expansion of the solid. Advantageously, the method requires no particular order of addition of the metal ion sources, and no subsequent heating, cooling, or pressing steps. Accordingly, the composition of the present invention is much simpler to prepare than existing metal salt-based biocides and may be, for example, placed into a suitable delivery container, such as a pipe, while still having a paste-like consistency and then solidified without significant expansion or shrinkage. The polymer matrix can be chosen to cause and accelerate the solidification of the composition, and to provide the desired dissolution rate when the composition is introduced into the water to be treated. The present invention achieves several significant advantages in this respect. It is easily solidified to a form that does not easily crumble or fall apart without the need for application of external pressure, e.g., in pelletizing or tableting steps. In addition, the crosslinked nature of the polymer matrix permits the material to dissolve in a relatively short period of time, rather than immediately, or over several months.

The present invention is also directed to a method for using the composition by contacting the composition with water in which microorganism growth is to be controlled. The composition is maintained in contact with the water for a sufficient time to dissolve the copper, silver, and zinc ion sources to the concentration needed to prevent or inhibit the growth of microorganisms. When the metal ion sources are immobilized in a crosslinked polymer matrix, such as chitosan or other polysaccharide, this matrix also dissolves in the water (although at a rate that is likely to be different from, and slower than, the dissolution rate of the ion sources) to obtain a concentration of dissolved polymer that helps to decrease the water's turbidity. This method can be used to treat, for example, water in swimming pools, hot tubs, spas, fountains, ponds, cooling systems, and humidification systems. The present invention is also directed to a water treatment system, which comprises the composition and a container that immobilizes the composition while allowing it to come into contact with the water to be treated. The container can be made from a variety of materials, and can assume a variety of forms, provided that water is permitted to flow in and out of the container and come into contact with the composition.

The primary purpose of the polymeric matrix is to provide a support for the metal ion sources, and to some extent to regulate their dissolution rate over a relatively short period of time, rather than to maintain the copper ion activity by sequestering it. As a result, there is no requirement to use an amount of polymer that dissolves to provide an aqueous concentration sufficient to sequester even a significant portion of the copper in solution. As an example, the ratio of crosslinkable polymer material to copper, calculated as elemental carbon and copper, can range from about 0.06:1 to about 0.74:1, more particularly from about 0.1:1 to about 0.5:1, even more particularly from about 0.2:1 to about 0.3:1.

As previously indicated, the present invention provides a number of advantages relative to current biocide compositions for the treatment of recirculating bodies of water, including inhibition of microbial and algal growth at reduced chlorine and copper levels. In contrast to known compositions, the present invention achieves a biocidal result using levels of copper below that at which staining occurs in normal recreational or industrial water systems. As a result, the present invention achieves a biocidal effect without staining surfaces in contact with the water, such as pool surfaces, and without increasing the turbidity of the water. Moreover, the present invention is prepared using a simple process which requires no special order of addition, no specific heating and/or cooling steps, and does not cause frothing or the formation of black deposits. The present invention is valuable in the control of microbial and algal contamination of swimming pools, and more generally, recirculating bodies of water. It provides a safe and economical alternative to the use of known metal salt-based biocides, while reducing the need for chlorine as a sanitizer.

DETAILED DESCRIPTION OF THE INVENTION

As previously indicated, the present invention is directed to an improved composition, water treatment system, and method for treating bodies of water to inhibit, or reduce the growth of microbes, algae, and/or fungi at reduced chlorine levels without noticeable staining. The composition is prepared by combining metal ion sources, including sources of copper, silver, and zinc ions, optionally with one or more crosslinkable polymers and a crosslinking agent. The presence of zinc and silver ion sources maintains an acceptable biocidal effect even in the presence of decreased amounts of copper and chlorine or hypochlorite. This reduces the risk of the formation of stains on surfaces in contact with water, and avoids turbidity of the water. The crosslinkable polymer and the crosslinking agent are selected so that, when crosslinked, the resulting composition releases ions into solution over a time period ranging from a few hours to several days to a year, and the resulting polymer matrix used to support the metal ion sources also dissolves to clarify the water. The invention is prepared by mixing the various components, forming the resulting composition into various shapes, and drying.

In more particular embodiments of the present invention, the copper ion source is employed in an amount, in percentage by weight based upon the total composition, ranging from about 16% to about 32%. In particular, the composition can comprise about 19% to about 26% copper ion source, more particularly, about 21% to about 24% copper ion source. The precise amount that is appropriate is dependent to some extent upon the source of the copper ion and its solubility in the water to be treated, but is significantly below the amount necessary to provide the same biocidal effect in the absence of silver or zinc ions. As discussed in more detail below, conventional copper-only biocides yield a copper ion concentration in typical swimming pool water of 0.5 to 1.0 ppm. Using the composition of the present invention (having an amount of copper ion source in the ranges above and having silver ion source and zinc ion source amounts as indicated below, and used in an amount of about 95 g/10000 gallons of water) provides an initial copper ion concentration of about 0.15 ppm or less, which decreases to a long term concentration of about 0.07 to 0.1 ppm over several days. Copper ion can be provided by any suitable copper-containing material known to yield copper ions in aqueous solutions at the expected temperature and pH of the water to be treated. In one aspect of the present invention, the source of copper ion is a soluble salt, such as copper sulfate, copper chloride, copper nitrate, copper bromide, copper fluoride, copper metaborate, copper ammonium carbonate, copper ammonium sulfate, copper oxalate, copper salicylate, copper acetate, copper formate, copper gluconate, or mixtures of these with each other or with other copper salts. The copper can also be present in its elemental form, in which case it enters the water by electrochemical reaction. Desirably, the source of copper ion is copper sulfate, as the sulfate anion can contribute to the polymerization or crosslinking of the monomer or crosslinkable polymer, respectively.

In a more particular embodiment of the present invention, the zinc ion source is employed in an amount, in percentage by weight based on the total composition, ranging from about 17% to about 70%. In particular, the composition can comprise an amount of zinc ion that can range from about 40% to about 67%, more particularly from about 55% to about 65%. The appropriate amount is dependent upon the source of zinc ion and its solubility in the water to be treated. The zinc ion source is typically used in an amount that provides an initial zinc ion concentration in the water to be treated of about 0.5 to about 0.6 ppm, which may decrease to a long term concentration of about 0.4 to about 0.45 ppm. Zinc ion can be provided by any compound known to yield zinc ions in aqueous solution at the expected pH and temperature of the water to be treated. In one aspect of the present invention, the source of zinc ion is a soluble salt, such as zinc sulfate (heptahydrate or monohydrate), zinc chloride, zinc nitrate, zinc bromide, zinc iodide, zinc borate, zinc fluoride, zinc acetate, zinc citrate, zinc acetylacetonate, zinc formate, zinc lactate, zinc oxalate, zinc salicylate, zinc laurate, zinc valerate, or mixtures of these with each other or with other zinc salts. The zinc can also be provided in its elemental form, in which case zinc ion enters the water by electrochemical reaction. Desirably, the source of zinc ions is zinc sulfate, as the sulfate anion can contribute to the polymerization or crosslinking of the polymer monomer or crosslinkable polymer, respectively.

In a more particular embodiment of the present invention, the silver ion source is used in an amount, in percentage by weight based upon the total composition, ranging from about 0.6% to about 12.5%. In a particular embodiment the composition of the present invention can comprise an amount of silver ion source in the range from about 2% to about 9%, more particularly from about 4% to about 7%. The appropriate amount is determined by the particular source of silver and its solubility in the water to be treated. The silver ion source can typically be used in an amount that provides a silver ion concentration in the water to be treated of about 0.3 to about 0.4 ppm initially, which decreases over time to about 0.01 to about 0.02 ppm. Silver ion can be provided by any suitable silver-containing compound that releases silver ions in aqueous solution at the expected pH and temperature of the water to be treated. In one aspect of the present invention, the source of silver ions is a soluble salt, such as silver nitrate, silver sulfate, silver fluoride, silver chlorate, silver perchlorate, silver tetraborate, silver acetate, silver benzoate, silver lactate, silver citrate, silver oxalate, or mixtures of these salts with each other or other silver salts. Silver can be provided as a single metal salt or a mixed metal salt composition. Silver can also be provided in its elemental form, where the silver ion enters the water by electrochemical reaction and/or dissolution of silver oxide. Desirably, the source of silver ion is silver nitrate or silver sulfate, more particularly silver nitrate, due to its favorable solubility.

In order to provide an appropriate level of ions to the water over an appropriate time period, it is desirable to combine copper sulfate, zinc sulfate, and silver nitrate as the respective ion sources in amounts within the ranges discussed above. As discussed above, the weight ratio of zinc ion source to copper ion source in the composition, calculated as elemental copper and zinc, can range from about 0.5:1 to about 4:1, more particularly from about 1:1 to about 3:1, even more particularly from about 2:1 to about 2.5:1. The weight ratio of silver ion source to copper ion source in the composition, calculated as elemental copper and zinc, can range from about 0.05:1 to about 2:1, more particularly from about 0.25:1 to about 1:1, even more particularly from about 0.5 1 to about 0.75:1.

The compositions according to the present invention are prepared by combining the metal ion sources discussed above with one or more crosslinkable polymers, which can then be crosslinked. The resulting polymer is temporarily crosslinked by anionic bridges, and forms a three-dimensional network or matrix that supports the metal ion sources, and immobilizes them to a certain extent, while allowing them to slowly dissolve into the water to be treated. In addition, the polymer matrix itself can clarify the water. While not wishing to be bound by any theory, it is believed that the polymer matrix, which desirably contains cationic moieties thereon, dissolves into the water over a period of a few days to a year, depending upon the amount of polymer added to the water. In quantities used in most swimming pool, hot tub, and spa applications, the composition is generally completely dissolved in well under three days in the water, and generally dissolves in a few hours. It is believed that the cationic moieties of the dissolved polymer molecules electrostatically attract and agglomerate colloidal and suspended particles in the water that individually are sufficiently small to avoid settling by precipitation and becoming trapped by the pool filter. These particles combine with the dissolved polymer to form agglomerates of sufficient size to be trapped by the pool filter, clarifying the water. Neither the dissolved polymer matrix nor the copper ion of the present invention are believed to be present in sufficiently high concentrations for the polymer to sequester significant amounts of copper ions.

The crosslinkable polymers are added to the composition in an amount ranging from about 4% to about 24% by weight based on the total composition. More particularly, the monomers or crosslinkable polymers may be added in an amount ranging from about 7% to about 13%, more particularly from about 8% to about 11% by weight. In one aspect of the invention, a crosslinkable polymer is used that comprises a chitosan compound, such as chitosan itself (which is a deacetylated chitin (a naturally occurring biopolymer) that is typically more than about 50% deacetylated), salts of chitosan, chitosan-gel, or mixtures of these. Mixtures of chitosan salt powders with chitosan salt gels have been found to provide good molding and casting properties to the resulting composition.

Other polymers suitable for forming the matrix of the solid composition according to the present invention include generally polymers that will solubilize in water relatively quickly, that contain amine moieties when dissolved in water, and that will form a solid when combined with the amounts of silver, copper, and zinc ion sources described above. Desirably, these polymers will not exhibit substantial expansion or shrinkage when combined with the above ion sources and dried to form a solid. Examples of suitable polymers include polysaccharides, including salts and derivatives of chitosan, such as chitosan acetate, chitosan lactate, chitosan glutamate, methyl-chitosan, N-carboxymethylchitosan, etc.

Desirably, a crosslinkable polymer is used that is a mixture of a chitosan salt and chitosan gel. The chitosan salt is desirably an easily prepared salt of chitosan, such as a salt of chitosan with a 1 to 18 carbon mono-or polycarboxylic acid, preferably chitosan acetate or chitosan lactate. Chitosan materials, including chitosan and chitosan salts, are commercially available from companies like Vanson, Aldrich, etc. The molecular weights of chitosans suitable for use in the present invention typically range from 5,000 to about 5,000,000. The level of deacetylation of the chitosan is generally not critical to the claimed invention, and chitosan of any degree of deacetylation available on the market can generally be used. However, chitosans having degrees of deacetylation above 50% are suitable due to their solubility characteristics. Salts of chitosan and lactic acid have been found to be effective as the crosslinkable polymer. The chitosan salt is typically added to the composition as a powder in an amount ranging from about 1% to about 5%, more particularly from about 2% to about 4%, even more particularly from about 2% to about 3%, by weight based on the total composition, and can be mixed with the metal ion sources during manufacture of the composition.

The chitosan can also be added in the form of a chitosan-gel, which can be added to the composition after mixing of the chitosan powder with the metal ion sources. Chitosan-gel is prepared by dissolving chitosan powder into a weak acid. Good results have been obtained by dissolving 4% by weight chitosan powder into 10% by weight of a weak acid, which may be citric acid, acetic acid, lactic acid, boric acid, or salicylic acid, especially citric acid.

The inclusion of both chitosan salt and chitosan-gel makes manufacture of the material significantly easier and contributes to the clarity of the water treated with the composition, as both function as water clarifiers. Specifically, chitosan-gel provides moisture to the composition that allows formation of a paste during manufacture, thereby allowing the composition to be easily extruded and/or formed into a variety of shapes, such as monoliths, pellets, tablets, or sticks. In addition, the chitosan-gel acts as a binder, which permits the composition to solidify. Chitosan salt powder provides additional chitosan to the composition while preventing it from getting too wet during manufacture. As a result, chitosan salt powder and chitosan-gel are advantageously used in combination, as described above. Specifically, chitosan powder alone may not produce sufficient binding of the composition, and the use of chitosan-gel alone may not allow the composition to dry to a solid when chitosan-gel is added at the level needed to act as a water clarifier.

The crosslinking agent added will depend upon the nature of the crosslinkable polymer used.

For example, when a chitosan polymer is used as described above, sulfuric acid is desirably employed in the composition as the crosslinking agent, and is typically added in an amount ranging from about 0.02% to about 0.05% by weight, based upon the total composition. The sulfuric acid aids the crosslinking of the chitosan and helps to solidify the composition. While not wishing to be bound by any theory, it is believed that crosslinking sulfate anions originating from sulfuric acid and sulfate salt sources make bridges between amino groups of chitosan polymeric chains. Combination of borate and phosphate anions can also be used, although phosphates are not desirable in a swimming pool environment, since they can promote formation of algae.

Carboxyl methyl-chitosan can be crosslinked with glutamic or aspartic acids or salts thereof The composition of the present invention is prepared by mixing the solid metal ion sources, including copper, silver, zinc ion sources, and any solid monomer or crosslinkable polymer, such as chitosan lactate, in powdered form in the appropriate amounts to form a homogeneous blend. For instance copper sulfate can be added in an amount of 16–32%, more particularly 19–26%, more particularly 21–24%, by weight (calculated as pentahydrate) based on the final composition. Silver nitrate can then be added in an amount of 0.6–12.5%, more particularly 2–9%, more particularly 4–7% by weight based on the final composition. Zinc sulfate can be added in an amount of 17–70%, more particularly 40–67%, more particularly 55–65% by weight (calculated as heptahydrate) based on the final composition.

As previously indicated, these materials can be added in any order. If powdered monomer or crosslinkable polymer is to be used, it can also be added at this point. For example, 1–5%, more particularly 2–4%, more particularly 2–3% chitosan lactate can be added to the above metal salts. These materials can then be blended to form a homogeneous blend using known and readily available mixing equipment and techniques, such as Mixmullers, Hobart mixers, and the like.

When chitosan lactate powder is used (i.e., chitosan is the crosslinkable polymer) chitosan-gel, prepared by dissolving chitosan powder into a weak acid, is then added to the blend. Chitosan-gel that has been prepared by dissolving 4% chitosan powder into 10% weak acid, such as citric acid, has been found to be suitable. However, as mentioned above, other weak acids, such as acetic acid, lactic acid, boric acid, and salicylic acid can be used. After addition of the crosslinkable polymer, any necessary crosslinking agents are added. When chitosan lactate and/or chitosan-gel are added as the crosslinkable polymers, sulfuric acid is used as the crosslinking agent. However, any crosslinking agent suitable for crosslinking the polymer used can be added. The resulting paste is then formed into the desired shape. For example, the composition can be cast in the form of tablets, pellets, granules, extrudates, or a monolith. The composition is then permitted to dry to a solid at room temperature and ambient humidity. Advantageously, no significant expansion or contraction in volume occurs during this process.

This simple preparation process results in a water treatment composition comprising a combination of metal salts disposed within a matrix of cross-linked polymers. The matrix is formed by polymerization of one or more monomers, followed by crosslinking, or by crosslinking of the crosslinkable polymer by the crosslinking agent. For instance, when the crosslinkable polymer is chitosan, the sulfate anions of both the zinc and copper sulfate salts, as well as sulfuric acid, contribute to the crosslinking. When placed in contact with water, metal ions comprising the present invention are leached from the composition over time. Components of the composition that are more slowly soluble, like the crosslinked chitosan, or that are relatively insoluble, are also released into the water, acting as water clarifiers. Chitosan and chitosan-gel are both effective water clarifiers, as discussed above. The preparation process is conducted under ambient temperature and pressure conditions, and no special precautions need to be taken.

In one aspect of the present invention, the composition is provided in conjunction with a container to form a water treatment system. The container can assume a variety of forms, provided that at least one water inlet opening and one outlet opening are present. The container may be simply a pipe having the solid composition disposed inside, with open ends, and optionally with some means for keeping the solid composition relatively immobilized within the pipe. For instance, the water treatment system may contain one or more screens, mesh, baskets, webs or baffles that prevents large particles or pieces of the composition from passing through, and keeps them within the pipe. In another embodiment, the container may in the form of a basket made of plastic or metal mesh, in particular molded plastic mesh. The mesh contains a plurality of openings of sufficient size to allow water to freely flow into and out of the basket, and thus come into contact with the composition inside, but to prevent large particles of the composition from leaving the basket. In one aspect of the invention, the closed basket is of a shape and size suitable for insertion into a swimming pool skimmer trap or leaf trap, or attachable to a cleaner moving about the pool.

In the practice of the present invention, the composition can be used to treat bodies of water, in particular recirculating bodies of water to inhibit microbial growth. Specifically, the composition can be used to treat swimming pools, hot tubs, spas, ponds, cooling water systems, humidification systems, fountains, etc. The composition and/or the water treatment system containing it, is desirably placed in the water in a way that will maximize the amount of water that comes into contact with the composition. For instance, the composition can be placed in the water in such a way that forced or natural currents or flow of the water brings water into contact with the composition. In a swimming pool, hot tub, or spa, this can be accomplished by placing the composition or water treatment system in the skimmer trap. An alternative is to place the composition or water treatment system near a pump outlet, so that recirculated water is continuously discharged near the composition and comes into contact with it. However, adequate results can be obtained by simply placing the water treatment system into the body of water and allowing it to move around in the water with any currents that exist. The solid composition is generally added in an amount of 95 g/10000 gallons of pool water. This will maintain an acceptable level of biocidal activity for 3 to 12 months.

While not wishing to be bound by any theory, it is believed that the composition of the present invention functions by allowing metal ion sources, which are soluble in water and are typically water soluble salts of the metal ion, to dissolve relatively quickly. The crosslinked polymer forms a structural matrix for supporting these salts, and regulates their dissolution to some extent. As time passes and embedded particles of salt near the surface of the solid dissolve, the structural polymer matrix becomes more porous, allowing water to access and dissolve particles of metal salts located within the solid material.

The use of the present invention does not require that the operation of the pool, hot tub, spa, cooling system, fountain, etc. be significantly modified, and normal water circulation rates, filtration, etc. should be unaffected. However, the addition of water treatment chemicals, such as chlorine or other halogen biocides, sequestrants, or copper biocides can be decreased substantially by using the present invention. For instance, the chlorine content of a typical swimming pool can be reduced to below 1 ppm, typically to around 0.5 ppm, a significant reduction from the 1–3 ppm required using conventional treatment systems.

Moreover, the amount of copper used in the composition of the present invention is significantly reduced when compared to that required by conventionally available copper biocides. For example, conventional copper-containing biocidal compositions for use in swimming pools provide a copper ion concentration in the pool water of 0.5 to 1.0 ppm, well above the industry accepted staining threshold. By contrast, the composition of the present invention generally provides an initial copper ion concentration of around 0.2 ppm, and this drops to a long term concentration (i.e., the concentration achieved after about 3 to 4 weeks of contact with the water) of around 0.08 to around 0.1 ppm, well below the accepted staining threshold. Without being bound by any theory, it is believed that the zinc and silver ions together provide an increased biocidal activity that decreases the need for copper ions. Because the zinc ion is nonstaining, and the silver and copper ions are present in amounts below those at which staining occurs, it is not necessary to add sequestering agents, such as EDTA, to avoid staining and precipitation. This also helps to avoid excessive binding of metal ions by the sequestrants and unexpected release of metal ions when the sequestrants are broken down by oxidants in the water.

The invention can be more clearly understood by reference to the following examples, which are not to be construed as limiting the invention in any way.

EXAMPLES

Example 1

179.3 g of $ZnSO_4.7H_2O$, 64.5 g of $CuSO_4.5H_2O$, 14.4 g of $AgNO_3$, and 7.2 g of chitosan lactate (Vanson) were mixed mechanically thoroughly. Chitosan gel was prepared by thoroughly mixing 4 g of chitosan powder (Aldrich, high molecular weight) in 100 ml of a 10% citric acid solution and heating slightly until dissolved. 22.1 g of this gel was mixed with the above metal salt/chitosan lactate mixture for a few minutes and to form a paste. 0.5 g of 25% $H_2SO_4$ was added to the paste and mixed thoroughly. The paste was left to dry overnight at 40° C. The product solidified into a rigid mass that neither shrank nor expanded during solidification. The resulting product was suitable for treating a 30,000 gallon swimming pool.

Example 2

A paste was made following the procedure described in Example 1, except that 191.2 g $ZnSO_4.7H_2O$, 69.1 g $CuSO_4.5H_2O$, 15.4 g $AgNO_3$, and 7.9 g of chitosan lact to make the initial salt mixture, to which was added 23.1 g of the chitosan gel described above, and 0.4 g of 25% $H_2SO_4$. 154 g of this mixture was inserted into a short copper pipe and left to dry overnight at room temperature. Again, the material dried without expansion or shrinkage. The pipe containing the dried materials was placed into the skimmer basket of a 13,500 gallon swimming pool. By the end of three days in the pool the materials were dissolved and the pipe was empty. The pool water remained crystal clear, and the pool surfaces were not stained for more than 2.5 months of an intensive swimming season, during which the free available chlorine level was held below 1 ppm. The conditions of this pool water is shown in Table I below.

| DATE OF SAMPLING | pH | FREE AVAILABLE CHLORINE (PPM) | Cu (PPM) | Ag (PPM) | Zn (PPM) |
| --- | --- | --- | --- | --- | --- |
| 6/10/97 (prior to treatment) | 7.29 | 0.99 | 0.021 | <0.006 | 0.029 |
| 6/13/97 | 7.41 | 0.06 | 0.191 | 0.034 | 0.489 |
| 6/20/97 | 7.35 | 0.67 | 0.182 | 0.025 | 0.505 |
| 6/27/97 | 7.70 | 0.56 | 0.163 | 0.028 | 0.516 |
| 7/8/97 | 7.81 | 0.08 | 0.115 | 0.018 | 0.489 |
| 7/14/97 | 7.80 | 0.25 | 0.099 | 0.024 | 0.426 |
| 7/29/97 | 7.73 | 0.21 | 0.088 | 0.027 | 0.431 |
| 8/14/97 | 7.49 | 0.10 | 0.077 | 0.028 | 0.431 |
| 8/25/97 | 7.65 | 0.03 | 0.079 | 0.019 | 0.415 |

While the invention has been described in detail in the above description, this should construed as limiting the invention, and other modifications and embodiments within irit of the invention are intended to be encompassed by the claims.

What is claimed is:

1. A composition for treating water, formed by preparing a mixture comprising:
   (a) a source of copper ion in an amount that provides a coper concentration in the water to be treated of about 0.2(b) a sour less;
   (b) a source of silver ion;
   (c) a source of zinc ion;
   (d) one or more cross-linkable polymers; and
   (e) a crosslinking agent and allowing the mixture to dry to a solid composition;
wherein the source of copper ion, the source of silver ion, and the source of zinc ion are present in amounts that provide a ratio of zinc ion source to copper ion source ranging from about 0.5:1 to about 4:1- and a ratio of silver ion source to copper ion source ranging from about 0.05:1 to about 2:1.

2. The composition according to claim 1, wherein the source of copper ion is present in an amount that provides an initial copper ion concentration in the water of about 0.2 ppm or less, and long term copper ion concentration of about 0.1 ppm or less.

3. The composition according to claim 1, wherein the source of copper ion is present in an amount that provides a copper ion concentration in the water to be treated of about 0.2 to about 0.07 ppm.

4. The composition according to claim 3, wherein the source of zinc ion is present in an amount that provides a zinc ion concentration in the water to be treated of about 0.5 to about 0.4 ppm.

5. The composition according to claim 4, wherein the source of silver ion is present in an amount that provides a silver ion concentration in the water to be treated of about 0.04 to about 0.01 ppm.

6. The composition according to claim 1, wherein the solid composition does not shrink or expand substantially as compared to the mixture before drying.

7. The composition according to claim 1, wherein the source of copper ion is selected from the group consisting of copper sulfate, copper chloride, copper nitrate, copper bromide, copper fluoride, copper metaborate, copper ammonium carbonate, copper ammonium sulfate, copper oxalate, copper salicylate, copper acetate, copper formate, copper gluconate, and mixtures thereof.

8. The composition according to claim 1, wherein the source of silver ion is selected from the group consisting of silver nitrate, silver sulfate, silver fluoride, silver chlorate, silver perchlorate, silver tetraborate, silver acetate, silver benzoate, silver lactate, silver citrate, silver oxalate, and mixtures thereof.

9. The composition according to claim 1, wherein the source of zinc ion is selected from the group consisting of zinc sulfate, zinc chloride, zinc nitrate, zinc bromide, zinc iodide, zinc borate, zinc fluoride, zinc acetate, zinc citrate, zinc acetylacetonate, zinc formate, zinc lactate, zinc oxalate, zinc salicylate, zinc laurate, zinc valerate, and mixtures thereof.

10. The composition according to claim 1, wherein the crosslinkable polymer (d) comprises a polysaccharide.

11. The composition according to claim 10, wherein the polysaccharide is a chitosan compound selected from the group consisting of chitosan, salts of chitosan with 1 to 18 carbon monocarboxylic acids, polycarboxylic acids, or both, methyl chitosan, N-carboxymethylchitosan, and mixtures thereof, and wherein the crosslinking agent is sulfuric acid.

12. The composition according to claim 11, wherein the chitosan compound is selected from the group consisting of chitosan, chitosan acetate, chitosan lactate, chitosan glutamate, methyl-chitosan, N-carboxymethylchitosan, and mixtures thereof.

13. The composition according to claim 12, wherein the chitosan is at least partially in the form of chitosan-gel.

14. The composition according to claim 13, wherein the chitosan compound is a mixture of chitosan lactate and chitosan-gel.

15. The composition according to claim 14, wherein the source of copper ion is copper sulfate and the source of zinc ion is zinc sulfate.

16. The composition according to claim 15, wherein the source of silver ion is selected from the group consisting of silver nitrate and silver sulfate.

17. The composition according to claim 16, wherein the source of silver ion is silver nitrate.

18. The composition according to claim 1, wherein the zinc to copper weight ratio is from about 1:1 to about 3:1.

19. The composition according to claim 18, wherein the zinc to copper weight ratio is from about 2:1 to about 2.5:1.

20. The composition according to claim 1, wherein the silver to copper weight ratio is from about 0.25:1 to about 1:1.

21. The composition according to claim 20, wherein the silver to copper weight ratio is from about 0.5:1 to about 0.75:1.

22. The composition according to claim 1, wherein the sources of copper, zinc, and silver ions are present in amounts that provide a zinc to copper weight ratio of from about 2:1 to about 2.5:1 and a silver to copper weight ratio of from about 0.5:1 to about 0.75:1, wherein both weight ratios are calculated based upon elemental copper, zinc, and silver.

23. The composition according to claim 1, wherein the crosslinkable polymer is present in an amount that provides a ratio of polymer to copper, calculated as elemental carbon and copper, of from about 0.06:1 to about 0.74:1.

24. The composition according to claim 23, wherein the ratio of polymer to copper is from about 0.1:1 to about 0.5:1.

25. The composition according to claim 24, wherein the ratio of polymer to copper is from about 0.2:1 to about 0.3:1.

26. A composition for treating water, formed by preparing a mixture comprising:
(a) about 16 to about 32% by weight copper sulfate (calculated as pentahydrate);
(b) about 0.6 to about 12.5% by weight silver nitrate;
(c) about 17 to about 70% by weight zinc sulfate (calculated as heptahydrate);
(d) about 1 to about 5% by weight chitosan salt;
(e) about 3 to about 19% by weight chitosan-gel; and
(e) about 0.02 to about 0.05% by weight sulfuric acid.

27. The composition according to claim 26, comprising:
(a) about 19 to about 26% by weight copper sulfate (calculated as pentahydrate);
(b) about 2 to about 9% by weight silver nitrate;
(c) about 40 to about 67% by weight zinc sulfate (calculated as heptahydrate);
(d) about 2 to about 4% by weight chitosan salt;
(e) about 5 to about 9% by weight chitosan-gel; and
(f) about 0.03 to about 0.04% by weight sulfuric acid.

28. The composition according to claim 27, comprising:
(a) about 21 to about 24% by weight copper sulfate (calculated as pentahydrate);
(b) about 4 to about 7% by weight silver nitrate;
(c) about 55 to about 65% by weight zinc sulfate (calculated as heptahydrate);
(d) about 2 to about 3% by weight chitosan salt;
(e) about 6 to about 8% by weight chitosan-gel; and
(f) about 0.04% by weight sulfuric acid.

29. The composition according to claim 26, wherein the chitosan salt is chitosan lactate.

30. The composition according to claim 26, wherein the chitosan-gel is prepared by dissolving 4% by weight chitosan powder into a 10% by weight solution of a weak acid.

31. The composition according to claim 30, wherein the weak acid is selected from the group consisting of citric acid, acetic acid, lactic acid, boric acid, and salicylic acid.

32. The composition according to claim 31, wherein the weak acid is citric acid.

33. A solid water treatment composition comprising:
(a) a matrix of soluble crosslinked polymer; and
(b) disposed within the matrix water soluble treatment materials comprising:
(1) a source of water soluble copper in an amount that provides a copper concentration in the water to be treated of about 0.2 ppm or less;
(2) a source of water soluble silver; and
(3) a source of water soluble zinc;
wherein the source of copper ion, the source of silver ion, and the source of zinc ion are present in amounts that provide a ratio of zinc ion source to copper ion source ranging from about 0.5:1 to about 4:1 and a ratio of silver ion source to copper ion source ranging from about 0.05:1 to about 2:1.

34. The composition according o claim 33, wherein the crosslinked polymer comprises a crosslinked polysaccharide.

35. The composition according to claim 34, wherein the crosslinked polysaccharide comprises crosslinked chitosan.

36. The composition according to claim 35, wherein the chitosan is at least partially crosslinked with sulfate anion moieties.

37. The composition according to claim 33, wherein the source of water soluble copper comprises copper sulfate.

38. The composition according to claim 33, wherein the source of water soluble zinc comprises zinc sulfate.

39. The composition according to claim 33, wherein the source of water soluble silver comprises silver nitrate.

40. The composition according to claim 33, which is in the form of tablets, pellets, sticks or one or more monoliths.

41. A solid water treatment composition comprising:
(a) a matrix of sulfur-crosslinked chitosan; and
(b) disposed within the matrix:
- (1) copper sulfate in an amount that provides a copper concentration in water to be treated of about 0.2 ppm or less.
- (2) silver nitrate; and
- (3) zinc sulfate; wherein the copper sulfate, silver nitrate, and zinc sulfate are present in amounts that provide a ratio of zinc sulfate to copper sulfate ranging from about 0.5:1 to about 4:1 and a ratio of silver nitrate to copper sulfate ranging from about 0.05:1 to about 2:1.

42. A method for treating bodies of water, comprising contacting the water with the composition according to claim 1 for a sufficient time to dissolve sufficient copper ion source, sufficient silver ion source, and sufficient zinc ion source to provide copper, silver, and zinc ion concentrations in the water sufficient to prevent or inhibit the growth of microorganisms and to decrease the turbidity of the water.

43. The method according to claim 42, wherein the water is swimming pool, hot tub, spa, fountain, pond, cooling system, or humidification system water.

44. A method for treating bodies of water, comprising contacting the water with the composition according to claim 33, for a sufficient time to control or inhibit the growth of micro organisms and to decrease the turbidity of the water.

45. The method according to claim 44, wherein the water is swimming pool, hot tub, spa, foutain, pond, cooling system, or humidification system water.

46. A composition for treating water, formed by preparing a mixture comprising:
(a) a source of copper ion, wherein the source of copper ion is present in an amount that provides a copper concentration in the water to be treated of about 0.2 ppm or less;
(b) a source of silver ion; and
(c) a source of zinc ion;
wherein the source of copper ion, the source of silver ion, and the source of zinc ion are present in amounts that provide a ratio of zinc ion source to copper ion source ranging from about 0.5:1 to about 4:1 and a ratio of silver ion source to copper ion source ranging from about 0.05:1 to about 2:1.

* * * * *

UNITED STATES PATENT AND TRADEMARK OFFICE
CERTIFICATE OF CORRECTION

PATENT NO. : 6,093,422
DATED : July 25, 2000
INVENTOR(S) : Denkewicz, Jr. et al.

It is certified that error appears in the above-identified patent and that said Letters Patent is hereby corrected as shown below:

Column 9,
Line 14, delete "0.5 1" and insert -- 0.5:1 --.

Column 13,
Delete the first line in Example 1 (line 33)
"179.3
g of $ZnSO_4.7H_2O$, 64.5 g of $CuSO_4.5H_2O$, 14.4 g"
and insert
--179.3 g of $ZnSO_4 \cdot 7H_2O$, 64.5 g of $CuSO_4 \cdot 5H_2O$, 14.4 g --.

In Example 2, delete the formula on lines 52-53
"191.2 g $ZnSO_4.7H_2O$, 69.1 g $CuSO_4.5H_2O$, 15.4 g $AgNO_3$,"
and insert
-- 191.2 g $ZnSO_4 \cdot 7H_2O$, 69.1 g $CuSO_4 \cdot 5H_2O$, 15.4 g Ag $NO_3$, --.

Line 53, delete "lact" and insert -- lactate were used --.

Column 14,
Line 18, "should construed" should be -- should not construed --.
Line 27, delete "0.2(b) a sour less" and insert -- 0.2 ppm or less --.
Line 31, a new paragraph should be inserted as follows:
"(e) a crosslinking agent and allowing the mixture to dry..."
should be:

-- (e) a crosslinking agent
and allowing the mixture to dry... --.

UNITED STATES PATENT AND TRADEMARK OFFICE
CERTIFICATE OF CORRECTION

PATENT NO. : 6,093,422
DATED : July 25, 2000
INVENTOR(S) : Denkewicz, Jr. et al.

It is certified that error appears in the above-identified patent and that said Letters Patent is hereby corrected as shown below:

Column 15,
Line 12, please delete "the" as follows:
    "wherein the crosslikable"
should be
    -- wherein crosslinkable --.

Signed and Sealed this

Fourteenth Day of August, 2001

*Attest:*

*Attesting Officer*

NICHOLAS P. GODICI
*Acting Director of the United States Patent and Trademark Office*